United States Patent
Barnhart et al.

(10) Patent No.: US 8,372,790 B2
(45) Date of Patent: *Feb. 12, 2013

(54) ANTIMICROBIAL HAND WASH

(75) Inventors: Ronald A. Barnhart, Clinton, OH (US); David P. Lerner, Akron, OH (US)

(73) Assignee: Gojo Industries, Inc., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/095,284

(22) Filed: Apr. 27, 2011

(65) Prior Publication Data

US 2011/0263471 A1     Oct. 27, 2011

Related U.S. Application Data

(62) Division of application No. 11/494,473, filed on Jul. 27, 2006, now abandoned.

(51) Int. Cl.
*A61K 7/50*     (2006.01)

(52) U.S. Cl. ........ 510/130; 510/136; 510/138; 510/156; 510/499

(58) Field of Classification Search ........................ None
See application file for complete search history.

(56) References Cited

U.S. PATENT DOCUMENTS

| | | | |
|---|---|---|---|
| 3,996,148 A | 12/1976 | Fusey | |
| 4,612,331 A | 9/1986 | Barratt | |
| 5,641,480 A | 6/1997 | Vermeer | |
| 5,712,232 A * | 1/1998 | Moriyama et al. | 510/120 |
| 5,972,860 A | 10/1999 | Eshita | |
| 6,479,442 B1 | 11/2002 | Berube | |
| 7,172,632 B2 | 2/2007 | Smith | |
| 7,517,842 B2 | 4/2009 | Barnhart | |

FOREIGN PATENT DOCUMENTS

| | | |
|---|---|---|
| WO | 9606152 | 2/1996 |
| WO | 0066079 | 11/2000 |

* cited by examiner

*Primary Examiner* — Necholus Ogden, Jr.
(74) *Attorney, Agent, or Firm* — Renner, Kenner, Greive, Bobak, Taylor & Weber

(57) ABSTRACT

An antimicrobial hand wash includes a soap, an antimicrobial agent, and an amine salt. The amine salt is found to increase the antimicrobial efficacy of the hand wash. The amine salt produced through the reaction of monoethanolamine and lactic acid is of particular interest as a soap addition. In processes of this invention, it is possible to create the desired amine salt in the soap in situ.

8 Claims, 1 Drawing Sheet

ANTIMICROBIAL HAND WASH

CROSS REFERENCE TO RELATED APPLICATION

This is a divisional application of application Ser. No. 11/494,473 filed Jul. 27, 2006, now abandoned, incorporated herein by reference.

TECHNICAL FIELD

The present invention generally relates to antimicrobial compositions, and, more particularly, relates to soaps that include an efficacy boosting chemical derived from the neutralization of a nitrogeneous base with a neutralizing acid.

BACKGROUND OF THE INVENTION

True soaps are created through a saponification reaction in which fats, more appropriately, fatty acids, are neutralized with a base. To ensure that the reaction is driven to completion, it is common practice to employ an excess of base. Because soaps are generally compatible with antimicrobial agents, they are often used in liquid antimicrobial hand washes. Such soap-based antimicrobial hand washes are found in numerous markets including healthcare, food services, and consumer.

Antimicrobial agents are selected from a variety of classes, including bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like p-chloro-m-xylenol (known as "pcmx") and 2,4,4'-trichloro-2' hydroxy-diphenylether (known as "triclosan"). Although these antimicrobial agents are used in numerous hand wash formulations, they are not without some detrimental properties. Antimicrobial agents are typically irritating to the skin. And while skin irritancy is a concern for any cosmetic or drug formulation, it is even more pertinent to hand washes because of the sensitivity of the body areas treated. There is a need to minimize the amount of antimicrobial agent present in a hand wash formulation, in order to minimize the irritancy thereof. But by reducing the amount of antibacterial agent present, it is expected that the antimicrobial properties of the hand wash will also be reduced, and, thus, there exist competing desires to reduce antimicrobial agents while maintaining antimicrobial efficacy.

Another important concern for a wash formulation is the aesthetics of the product. For example, the public has come to associated foaming ability with cleaning ability, and, as a result, consumers are less likely to purchase a wash formulation that does not foam while washing. This consumer perception drives those in the market to formulate washing products which produce copious amounts of foam. As mentioned above, irritancy is a concern. The color and odor of a wash formulation is also important. When soaps are used in conjunction with antimicrobial agents, they do not present the best of each of these desired properties. Although the presence of the soap allows for a reduction in the amount of antimicrobial agent while maintaining a relatively high log kill, antimicrobial soap products tend to irritate the skin. Thusly, skin conditioning agents need added to produce an aesthetically pleasing hand wash.

SUMMARY OF THE INVENTION

This invention involves the creation of a soap through a saponification reaction and the creation of an amine salt for inclusion in the soap. Herein, "primary" relates to those acids and bases employed in the saponification reaction, while "secondary" relates to those acids and bases employed to create the amine salt, although, when a nitrogenous base is employed, it can serve as both the primary and the secondary base. "Nitrogenous base" refers to bases that include at least one nitrogen bound to no more than three substituents.

In one embodiment, this invention provides an antimicrobial hand wash comprising a soap and the reaction product of a nitrogenous base neutralized with a neutralizing acid selected from anhydrides, organic acids, and inorganic acids.

In another embodiment, this invention provides an antimicrobial hand wash comprising a soap; an antimicrobial agent; and the reaction product of monoethanolamine neutralized with lactic acid.

In a process in accordance with this invention, an antimicrobial hand wash is created by combining a fatty acid with a nitrogenous base to produce a soap and an excess of base, and neutralizing the excess base with a neutralizing acid selected from the group consisting of acetic acid, lactic acid, glycolic acid, acetylsalicylic acid, nicotinic acid, benzoic acid, isopropanoic acid, oxalic acid, succinic acid, benzoic acid anhydride, mixed phosphoanhydride, and mixtures thereof.

DETAILED DESCRIPTION OF THE PREFERRED EMBODIMENT

Figure 1:
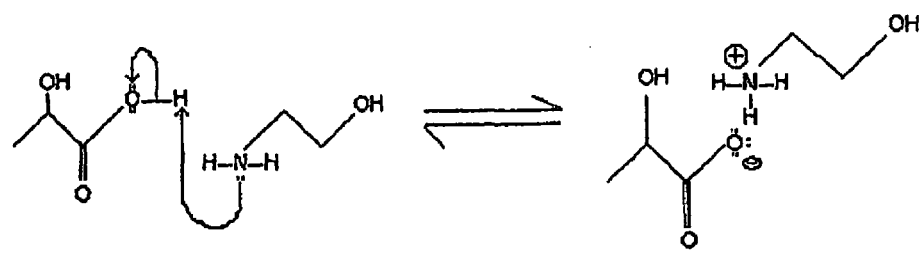
FIG. 1 is a hypothesized reaction between lactic acid and monoethanolamine, in accordance with an embodiment of this invention reduced to practice.

The hand wash herein includes a soap; an antimicrobial agent; and an amine salt. The soap is made through a saponification reaction between a primary fatty acid and a primary base. The amine salt is created through the neutralization of a nitrogenous base with a secondary acid.

The primary base may be a hydroxide; a nitrogenous base; an oxide of a group I element, calcium, strontium, or barium; or the conjugate base of a weak acid. As will be seen herein, the selection of the primary base can affect the process methods that can be practiced to produce the hand wash. With nitrogenous bases, the amine salt may be created either by neutralizing excess primary nitrogenous base left over after completion of the saponification reaction, in which case it is present in the soap, at creation, or by neutralizing the same primary nitrogenous base or a different secondary nitrogenous base in a separate process, in which case it is subsequently added to the soap created in the saponification reaction. If the primary base is chosen to be a hydroxide; an oxide of Group I, calcium, strontium, or barium; or the conjugate base of a weak acid, the amine salt cannot be created by neutralizing an excess of that base, and a secondary nitrogenous base is neutralized to create the amine salt.

A secondary acid is employed to neutralize the excess nitrogenous base or secondary nitrogenous base as the case may be. Thus, as already stated, "primary" relates to those acids and bases employed in the saponification reaction, while "secondary" relates to those acids and bases employed to create the amine salt, although, when a nitrogenous base is employed, it can serve as both the primary and the secondary base. The amine salt created via the acid-base neutralization between the secondary acid and either an excess primary nitrogenous base or a secondary nitrogenous base is found to have surprising antimicrobial properties when combined with an antibacterial agent.

The soap is made from a primary fatty acid and a primary base. The primary fatty acid may be derived from crude fats or selected carboxylic acids, although it is typically less desirable to employ the crude fats. The crude fats include known animal fats, vegetable oils and the like, and generally have a glycerol linked with at least 1, but no greater than three fatty acids. The carboxylic acids, which are more preferred, may be selected from carboxylic acids having from 6 to 40 carbon atoms in the main fatty chain. In other embodiments, the carboxylic acids are chosen to have from 6 to 20 carbon atoms in the main fatty chain. Suitable carboxylic acids include, and are not limited to, arachidic acid, arachidonic acid, beeswax acid, behenic acid, coconut acid, corn acid, cottonseed acid, erucic acid, hydrogenated coconut acid, hydrogenated menhaden acid, hydrogenated palm acid, hydrogenated tallow acid, hydroxystearic acid, isomerized linoleic acid, isomerized safflower acid, isostearic acid, lauric acid, linoleic acid, myristic acid, oleic acid, olive acid, palm acid, palmitic acid, palm kernel acid, peanut acid, pelargonic acid, rapeseed acid, rice bran acid, ricinoleic acid, safflower acid, soy acid, stearic acid, sunflower seed acid, tall oil acid, tallow acid, undecanoic acid, undecylenic acid, and wheat germ acid. Mixtures of the forgoing might also be employed. In particular embodiments, lauric acid is preferred.

Various primary bases can be selected for the saponification reaction, including hydroxides, nitrogenous bases, oxides of Group I, Ca, Sr, or Ba, and conjugate bases of weak acids. A nitrogenous base is ultimately employed to create the desired amine salt component of the hand wash, and thus if a nitrogenous base is not employed as the primary base for the saponfication reaction, one must be employed as a secondary base to create the amine salt. If a nitrogenous base is used as the primary base, the amine salt can be formed directly in the soap solution. More particularly, an excess of nitrogenous base can be used in the saponification reaction, and, once that reaction is complete, the excess can be neutralized by a secondary acid to create the amine salt in situ. The processes for creating the hand wash are disclosed more fully below.

The nitrogenous base, whether primary or secondary, can be selected from ammonia and virtually any hydroxylated nitrogenous base. Suitable nitrogenous bases include, but are not limited to, 2-aminobutanol, aminoethyl propanediol, aminomethyl propanol, aminopropanediol, bis-hydroxyethyl tromethamine, butyl diethanolamine, butylethanolamine, dibutyl dthanolamine, diethanolamine, diisopropanolamine, diisopropylamine, dimethyl isopropanolamine, monoethanolamine, dimethyl monoethanolamine, ethyl ethanolamine, isopropanolamine, isopropylamine, methylethanolamine, methylglucamine, morpholine, triethanolamine, triisopropanolamine, tromethamine. Mixtures of the forgoing might also be employed. In particular embodiments, monoethanolamine is preferred.

The other primary bases suitable for use include hydroxides such as calcium hydroxide, lithium hydroxide, potassium hydroxide, and sodium hydroxide; metal oxides such as calcium oxide, and sodium oxide; and conjugate bases of weak acids such as dipotassium phosphate, disodium phosphate, magnesium carbonate, pentapotassium triphosphate, petnasodium trisphosphate, potassium carbonate, sodium carbonate, tetrapotassium pyrophosphate, tetrasodium pyrophosphate, and trisodium phosphate. If one or more of these other primary bases is employed as the primary base, and there is not sufficient excess nitrogenous base (if any) employed, the nitrogenous base is to be employed as a secondary base.

The secondary acid used to neutralize either an excess of nitrogenous base or a secondary nitrogenous base may generally be selected from the acid classes of anhydrides and organic and inorganic acids. Appropriate organic compounds include, but are not limited to, carboxylic acids, organic acid anhydrides and mixed acid anhydrides. A non-exhaustive list of useful secondary acids as neutralizing agents includes linear carboxylic acids such as acetic acid, lactic acid, and glycolic acid; homocyclic carboxylic acids such as acetylsalicylic acid; hetrocyclic carboxylic acids such as nicotinic acid; aromatic carboxylic acids such as benzoic acid; branched aliphatic carboxylic acids such as isopropanoic acid; polyprotic carboxylic acids such as oxalic acid and succinic acid; and organic and mixed anhydrides such as benzoic acid anhydride and mixed phosphoanhydride. Suitable inorganic acids may include, but are not limited to, strong and weak polyprotic acids such as sulfuric acid and phosphoric acid; monoprotic weak acids such as sodium bisulfate; monoprotic strong acids such as hydrogen halides and perchloric acid; and inorganic acid anhydrides such as carbon dioxide. In particular embodiments, lactic acid is most preferred.

The antimicrobial hand wash contains at least one antimicrobial agent, which is generally appreciated as a term of art for those compounds that produce acceptable time-kill antimicrobial activity to be suitable for sanitizing. More specifically, the hand wash herein has efficacious properties against both Gram-positive and Gram-negative microorganisms. For purposes of this disclosure, the terms "antimicrobial agent" is to cover compositions that have greater than 2 log kill reduction on both Gram-negative bacteria, specifically *Klebsiella pheumoniae*, and Gram-positive bacteria, specifically *Staphylococcus aureus*.

In particular embodiments, the antimicrobial agent of the hand wash is selected from the group consisting of bis-guanidines, quaternary ammonium compounds, benzyl alcohols, trihalocarbanilides, iodine containing compounds, and phenolic compounds. Mixtures of the forgoing might also be employed. In particular embodiments, phenolic compounds are employed.

The phenol-based antimicrobial agents useful in this invention are exemplified by the following compounds, and may be used alone or in combination:

(a) 2-Hydroxydiphenyl Compounds

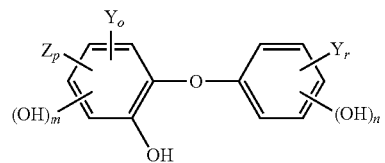

wherein Y is chlorine or bromine, Z is $SO_2H$, $NO_2$, or $C_1$-$C_4$ alkyl, r is 0 to 3, o is 0 to 3, p is 0 or 1, m is 0 or 1, and n is 0 or 1. In preferred embodiments, Y is chlorine or bromine, m is 0, n is 0 or 1, o is 1 or 2, r is 1 or 2, and p is 0. In especially preferred embodiments, Y is chlorine, m is 0, n is 0, o is 1, r is 2, and p is 0. A particularly useful 2-hydroxydiphenyl compound has the structure:

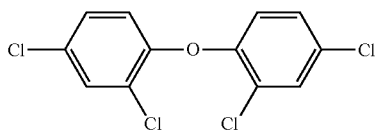 [SMILES: Clc1ccc(Oc2ccc(Cl)cc2Cl)c(Cl)c1]

having the adopted name, triclosan, and available commercially under the tradename IRGASAN DP100, from Ciba Specialty Chemicals Corp., Greensboro, N.C. Another useful 2-hydroxydiphenyl compound is 2,2'-dihydroxy-5,5'-dibromodiphenyl ether. Additional bisphenolic compounds are disclosed in U.S. Pat. No. 6,113,933, incorporated herein by reference.

(b) Phenol Derivatives

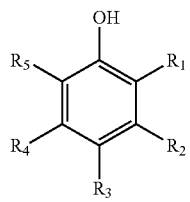

wherein $R_1$ is hydro, hydroxy, $C_1$-$C_4$ alkyl, chloro, nitro, phenyl, or benzyl; $R_2$ is hydro, hydroxy, $C_1$-$C_6$ alkyl, or halo; $R_3$ is hydro, $C_1$-$C_6$ alkyl, hydroxy, chloro, nitro, or a sulfur in the form of an alkali metal salt or ammonium salt; R.sub.4 is hydro or methyl; and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in WO 98/55096 and U.S. Pat. No. 6,113,933, incorporated herein by reference.

(c) Diphenyl Compounds

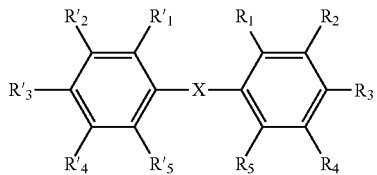

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5, 5',6, 6'-hexachlorodiphenyl sulfide, and 3,3'-dibromo-5,5'-dichloro-2,2'-dihydroxydiphenylamine. Other diphenyl compounds are listed in WO 98/55096, incorporated herein by reference.

In particular embodiments, the phenol-based antimicrobial agent is selected from triclosan, 2,2'-dihydroxy-5,5'-dibromodiphenyl ether, pcmx, ortho-phenylphenol, and mixtures thereof.

As known, additional compounds are typically used to produce an acceptable hand wash for consumer use. These compounds include, but are not limited to, foam modifying agents, pH adjusting agents, emollients, humectants, skin conditioning agents, dyes and fragrances. Herein, they may be employed in amounts and for reasons known in the prior art.

There are two processes by which the hand wash of this invention might be created. In accordance with a process that is described herein as "super basing," the saponification reaction between the primary nitrogenous base and the primary fatty acid is carried out in an aqueous solution with an excess of primary nitrogenous base. Although it is normal for saponification reactions to be carried out with an excess of base present, this invention adds to this general practice by creating an amine salt from the excess base in situ. After the saponification is complete, excess base is backtitrated with the secondary acid to create the amine salt directly within the soap solution. In accordance with a process that is described herein as "equivalent saponification," the saponification reaction is carried out with near equivalence of primary nitrogenous base and primary fatty acid, such that there is not a significant excess of the primary base present after saponification. The amine salt is added to the soap solution rather than being created therein, as in the super dosing process.

In the super dosing process, which employs a primary nitrogenous base and a primary fatty acid in the saponification reaction, the mole to mole ratio for alkalinity to free fatty acid is preferably from about 1.5:1 to 3:1, as opposed to the 0.8:1 to 1.25:1 ratios generally practiced in saponification reactions. After completion of the saponification, the excess nitrogenous base is backtitrated with a second acid to an alkalinity to total acid ratio from about 0.8:1 to 1.25:1, wherein "total acid ratio" takes into account the number of moles of both the primary fatty acid employed in the saponification reaction and the secondary acid employed to create the amine salt. These ratios are preferred only. It should be appreciated that to the amine salt could be produced to be present in virtually any amount, although the disclosed ratios are preferred due to cost considerations.

In the equivalent saponification process, the mole to mole ratio for alkalinity to free fatty acid is substantially 1:1, such that there is an insubstantial amount of excess base at the completion of the saponification reaction. This process is most likely used when the primary base employed is not a nitrogenous base, and thus cannot contribute to provide the amine salt in situ as in the super dosing process. The amine salt can either be created in a separate process, or even purchased, and added to the soap solution, or it can be created by adding a secondary nitrogenous base to the soap solution and thereafter neutralizing it with a secondary acid. Although, again, the amine salt could be added to be present in virtually any amount, it is preferable added to comprise up to about 20% of the final hand wash formula, by weight.

For either saponification technique the pH of the solution should be similar. The preferred pH is between 7 and 10.5.

The invention goes against common day teachings by using a large amount of excess base, and then the excess base is titrated with a second acid to an alkalinity to total acid ratio from about 0.8:1 to 1.25:1. Normal saponification processes occur at alkalinity to fatty acid ratio from about 0.8:1 to 1.25:1.

If the antimicrobial agent has a limited solubility in water, as is the case, for example, with phenol derivative antimicrobial agents, the antimicrobial agent is added to the soap solution as part of an "active premix," which is a solution of the antimicrobial agent dissolved in a hydric solvent. The hydric solvent should be chosen from either monohydric solvents, such as alcohols, or polyhydric solvents, such as glycols. The most preferred compounds are short carbon chain polyhydric compounds, on the order of eight or less carbons, but longer chains can be used. The sole use of the solvent is to dissolve the antimicrobial agent; it is therefore pertinent that the solvent have the ability to readily dissolve the desired antimicrobial agent or agents. The antimicrobial agent, whether in a premix or alone, may be added anytime after the completion of the saponification reaction. In accordance with particular embodiments, the antimicrobial agent comprises from about 0.01 to 10 wt % of the final formula; in other embodiments, from 0.05 to 7.5 wt %; and in yet other embodiments, from 0.1 to 1 wt %.

The hand wash formulations of this invention are typically comprised of from about 0.01 to 17.5 weight percent (wt %) of the primary fatty acid; from about 0.005 to 25 wt % of the primary base; and from about 0.01 to 10 wt % of the antimicrobial agent. In particular embodiments, the primary fatty acid comprises from about 0.05 to 17.5 wt % of the final formula, and in yet other embodiments, from about 0.1 to 15 wt %. In particular embodiments, the primary nitrogenous base comprises from about 0.025 to 25 wt % of the final formula; in other embodiments, from about 0.05 to 22 wt %. The secondary base, whether it is the same as the primary base or not, can be identified as any amount of base that exceeds that needed for equivalent saponification. The secondary base is from about 0.005 to 22.5 wt %, in yet other embodiments, from about 0.025 to 22.5 wt %, and more particular from about 0.05 to 20 wt %. The secondary acid comprises from about 0.008 to 25 wt %, in yet other embodiments from about 0.04 to 25 wt %, and more particular from about 0.09 to 22.5 wt % of the hand wash formula.

In accordance with a particular embodiment reduced to practice, monoethanolamine is both the primary and secondary base, and it is reacted with lactic acid as the secondary acid to produce an amine salt, believed to be monoethanolammonium lactate. FIG. 1 shows the chemical reaction. As pictured the acid and base react in a one mole to one mole ratio. Lactic acid is a monoprotic acid, and this proton is the one transferred during this reaction, creating a carboxylate anion. The amine group found in monoethanolamine accepts the proton from the lactic acid via the lone pair of electrons on the nitrogen. This proton then creates an ammonium cation.

The reaction occurs spontaneously, and there is one distinct characteristic of the reactants that determine the quality of this reaction that need to be examined. First, the reaction generates heat and the temperature needs to be monitored because of detrimental effects at high temperatures. With higher temperature, the oxidation of monoethanolamine via the loss of the amine group is expedited. The reaction should be carried out slowly so the heat generated can dissipate and not degrade the monoethanolamine. This can be a concern with other nitrogenous bases, and should be taken into account to avoid negatively impacting the reaction.

For the generation of just the amine salt, the pH is determined by a complex equilibrium between both the weak conjugate base and weak conjugate acid of the product. Monoethanolammonium will donate the proton picked up from the lactic acid to water. Also, the absorption of a proton via the negative portion of lactic acid occurs. The derivation of the equation to calculate the pH based on the acid and base used to create the salt is shown below:

B represents monoethanolamine and A represents lactate

Beginning with the conjugate acid dissociation:

| 1. $BH^+ + OH^- \leftrightarrow B + H_2O$ | $[B]/([OH^-] * [BH^+])$ | $1/K_b$ |

Consider the disassociation of water:

| 2. $H_2O + H_2O \leftrightarrow OH^- + H_3O^+$ | $[OH^-] * [H_3O^+]$ | $K_w$ |

Combine equation 1 and 2:

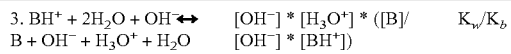
| 3. $BH^+ + 2H_2O + OH^- \leftrightarrow B + OH^- + H_3O^+ + H_2O$ | $[OH^-] * [H_3O^+] * ([B]/[OH^-] * [BH^+])$ | $K_w/K_b$ |

The like terms cancel leaving:

| 4. $BH^+ + H_2O \leftrightarrow B + H_3O^+$ | $([H_3O^+] * [B])/[BH^+]$ | $K_w/K_b$ |

Now consider the disassociation of the acid:

| 5. $HA + H_2O \leftrightarrow A^- + H_3O^+$ | $([A^-] * [H_3O^+])/[HA]$ | $K_a$ |

Combine equations 4 and 5:

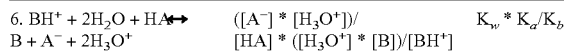
| 6. $BH^+ + 2H_2O + HA \leftrightarrow B + A^- + 2H_3O^+$ | $([A^-] * [H_3O^+])/[HA] * ([H_3O^+] * [B])/[BH^+]$ | $K_w * K_a/K_b$ |

[A−] is equal to [BH+] at the equivalence point and assert that [HA] is equal to [B]

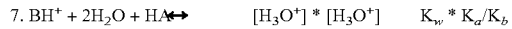
| 7. $BH^+ + 2H_2O + HA \leftrightarrow B + A^- + 2H_3O^+$ | $[H_3O^+] * [H_3O^+]$ | $K_w * K_a/K_b$ |

Manipulate the equation to produce the pH of the solution:

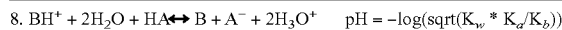
| 8. $BH^+ + 2H_2O + HA \leftrightarrow B + A^- + 2H_3O^+$  pH = $-\log(\text{sqrt}(K_w * K_a/K_b))$ |

Figure 2:
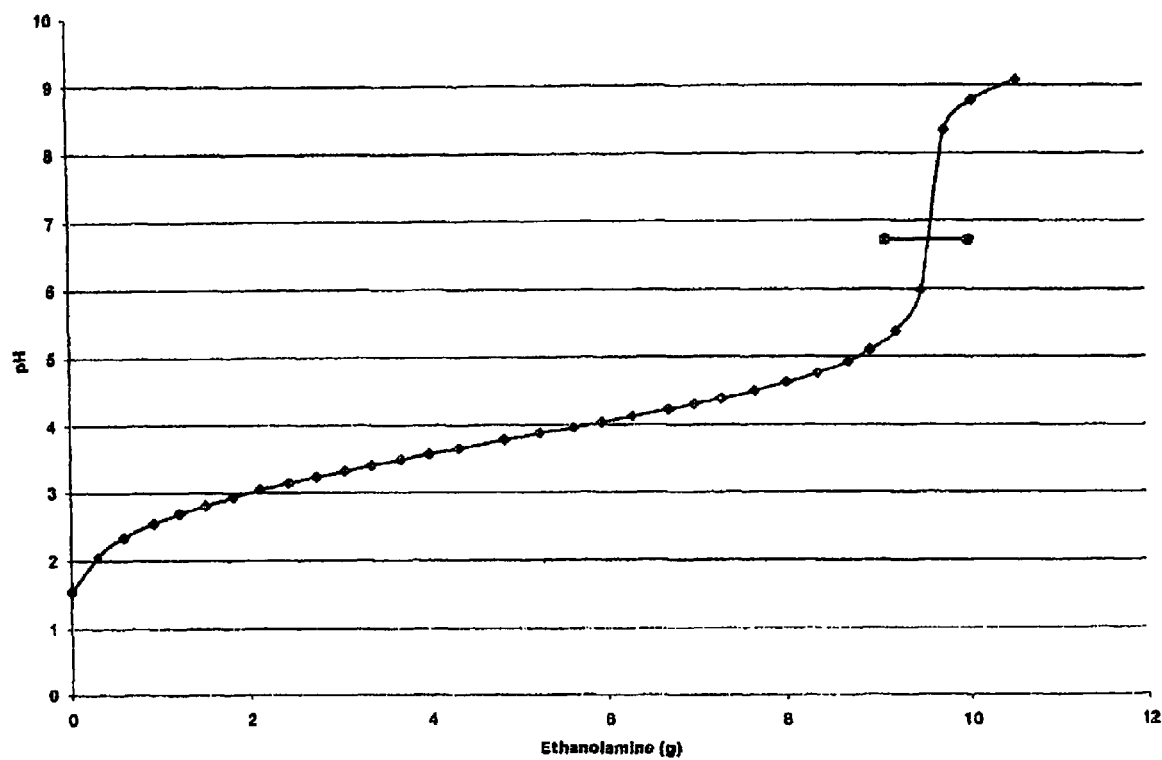
FIG. 2 is a titration curve for monoethanolamine-lactic acid neutralization that experimentally verifies the correctness of the equation derived herein below respecting such neutralization.

Per the preferred embodiments, lactic acid, $pK_a$ of 3.86, and monoethanolamine, $pK_b$ of 4.56, the pH at the equivalence point should be 6.65. This is experimentally verified in FIG. 2. Because of the spontaneity of the reaction the ratio of acid to base can be in any proportion, although near equivalence is most desired.

The resulting solution varies slightly in appearance depending on the reaction conditions. If the reaction is carried out slowly and the heat is allowed to dissipate the solution can be colorless, but if the reaction is done quickly and heat builds up, then the solution will turn to an amber color because of the oxidation of monoethanolamine. The solution also has a slightly honey-like odor. One inherent observation is an increase in the viscosity of the solution. Starting from two water thin liquids, the final solution has a viscosity of about 1500 to 3000 centipoise.

Although there are numerous antimicrobial agents, the most preferred embodiment contains halogenated diphenylether. Most specifically, the use of pcmx and/or triclosan is most desired. These two compounds, and most specifically triclosan, interact with the amine salt to produce a more efficacious hand wash. The hypothesis governing this trend is described as charge interaction between the negatively charged triclosan substitutents, chlorines and the hydroxyl group, and the positive charge found on the amine group. Triclosan has a $pK_a$ value of 7.4, so, at the desired pH of the hand wash, the triclosan will be disassociated and have a negative charge. The positive charge on the amine is attracted to the negative charge on the triclosan and, thus, the triclosan is chelated and prevented from precipitating.

The antimicrobial properties of the hand wash containing an amine salt are improved compared to hand washes without. This improvement is seen both in the broad spectrum inhibition and the quick inhibition. A log reduction of 2 on hard to kill organisms, specifically Staphylococcus aureus (MRSA) (ATCC# 33591) at 30 second exposure time, is desired and, as such, this hand wash provides greater than 2 log reduction of both the Gram positive Staphylococcus aureus (MRSA) (ATCC# 33591) and Shigella dysenteriae (ATCC# 13313).

EXPERIMENTAL

Example 1

While making soap through a saponification reaction of a primary nitrogenous base with a primary fatty acid, the addition of excess base was examined. Because the high pH resulting from excess base would be irritating and detrimental to the skin care properties of the hand wash, the excess base was neutralized with a second water soluble acid. For a first control (Control 1), a hand wash made without excess base was tested along side the hand wash containing excess base neutralized with the second acid. A second control (Control 2) excess base is present, but is not subsequently neutralized with the second acid. The hand washes included antimicrobial agent, namely triclosan. The base was monoethanolamine. The first acid was lauric acid, and the second was lactic acid.

The triclosan was dissolved in dipropylene glycol, to make an "active premix." The monoethanolamine was added to the water and then the lauric acid was added. After allowing the saponification process to complete, lactic acid was added to neutralize the excess base, and was added until the solution was brought to a pH of 9.25. The active premix was then added to the solution to create the antimicrobial hand wash. The ingredient amounts were as follows:

|  | Excess Base: | Control 1 | Control 2: |
|---|---|---|---|
| Water | q.s. to 100 g | q.s. to 100 g | q.s. to 100 g |
| Lauric Acid | 5 g | 5 g | 5 g |
| Monoethanolamine | 3.833 g | 1.7 g | 3.833 g |
| Lactic Acid | q.s. to pH 9.25 | N/A | N/A |
| Dipropylene Glycol | 3 g | 3 g | 3 g |
| Triclosan | 0.3 g | 0.3 g | 0.3 g |
|  | pH: 9.22 | pH: 9.21 | pH: 10.30 |

A log reduction test was performed for each formulation. The samples were tested by placing a loopful (approx 10 microliters) of the formulation into a microbial broth (Staph. Aureus ATCC# 6538) for 15 seconds. A sample was then taken from the broth and plated. The bacteria was grown and then counted resulting in a quantitative reduction value, as shown below.

Control 1: log reduction 0.6
Excess Base: log reduction 4.0
Control 2: log reduction 1.3

There is a dramatic increase in the log reduction for the antimicrobial hand wash employing excess base subsequently neutralized with a second acid. This suggests that the neutralized excess base improves the antimicrobial properties of the hand wash.

Example 2

Because there is a boost in the efficacy of the product due to the use of excess primary nitrogenous base and a secondary neutralizing acid, alternate bases were tested. The focus was to find suitable weaker bases that might be used, because weaker bases should further reduce the degree of skin irritation experienced when using a resultant antimicrobial hand wash. Samples were made using the same procedure as in Example 1, but with alternate bases. Because the bases had different molecular masses, the percentage used in each sample was different. This was done in order to ensure that the same number of moles were present in each sample, thus allowing for the same concentration of amine salt in the final hand wash. As mentioned the same formulation was used as in Example 1, but with the base, monoethanolamine, replaced with the following:

Alternate Bases

| | | |
|---|---|---|
| Triethanolamine | 9.355 g | Equistar, USA |
| Aminomethylpropanol (AMP-95) | 5.525 g | ANGUS Chemical, USA |
| Tetrahydroxypropyl ethylenediamine (Neutrol TE) | 10.29 g | BASF, USA |

Log reductions were calculated as follows:

| | |
|---|---|
| Triethanolamine hand wash | 4.1 |
| AMP-95 hand wash | 1.4 |
| Neutrol TE hand wash | 1.7 |

Despite having better skin compatability due to the fact that they employ weaker bases, the log reductions for these antimicrobial hand washes were not as high as that for the monoethanolamine-based antimicrobial hand wash of Example 1.

Example 3

In this example, alternate acids were considered for use in neutralizing excess base present after the saponification reaction, i.e, to replace the lactic acid specifically used in Example 1. The samples were made in accordance with Example 1, except that the lactic acid was replaced with alternate acids. A sample was also created having excess base and no second acid addition. The samples were adjusted to pH: 9.2+/−0.10 with each acid, and then tested for log reduction properties. The acids tested were as follows:

| Acid | Amount | pH | Log Reduction |
|---|---|---|---|
| None | N/A | 10.15 | 1.6 |
| Hydrochloric acid | 47.66 g | 9.19 | 3.1 |
| Phosphoric acid | 1.52 g | 9.17 | 3.5 |
| Sulfuric acid | 12.20 g | 9.18 | 3.4 |
| Ascorbic acid | 4.68 g | 9.17 | 4.4 |
| Malic acid* | 1.87 g | 9.12 | 2.8 |
| Succinic acid | 1.75 g | 9.17 | 2.8 |
| Glycolic acid | 2.04 g | 9.16 | 3.0 |
| Acetic acid | 43.68 g | 9.19 | 2.2 |

From the high pH sample, it is plain to see the amine salt is important for the efficacious properties of the hand wash. Of the different acids tested, all drastically improved the log reduction values for the hand wash. The hydrochloric, sulfuric, and acetic acid required large amounts of acid because the two solutions were dilute compared to the other acids (either concentrated in solution or crystals).

Experiment 4

In this example, tests were run to determine whether the base neutralized with the second amine acid (i.e., the amine salt) must be created in the hand wash from excess base left over from an initial saponification reaction or if it could be added as a separate addition to a soap solution produced without excess base. Monoethanolamine and lactic acid were neutralized in water in a separate "neutralization solution," i.e., the monoethanolamine is not present as excess in a saponfication reaction. The neutralization solution was made as follows:

| | |
|---|---|
| 122.34 g | Water |
| 45.81 g | Monoethanolamine |
| 76.90 g | Lactic acid |

The monoethanolamine was dissolved in the water, and the lactic acid was slowly added to the solution, because, if added too quickly, the heat not dissipated from the neutralization reaction would degrade the monoethanolamine. The degradation can be seen by a color change from a clear colorless mixture to a dark amber hue. A hand wash was made per Example 1 procedures, but without excess base (monoethanolamine). The solution was then split into four separate solutions so that the neutralization solution could be added in differing amounts.
Hand Wash Formula

| | |
|---|---|
| Water | q.s. to 100 g |
| Lauric Acid | 5 g |
| Monoethanolamine | 1.7 g |
| Dipropylene Glycol | 3 g |
| Tricloan | 0.3 g |
| Neutralization solution | See Table below. |

| Sample | Amount Formula | Amount Neutralization solution | Amount water | Log Reduction |
|---|---|---|---|---|
| A | 87.2 g | 12.8 g | 0 g | 4.7 |
| B | 87.2 g | 6.4 g | 6.4 g | 3.7 |
| C | 87.2 g | 3.2 g | 8.6 g | 3.1 |
| D | 87.2 g | 0 g | 12.8 g | 2.1 |

The amount of monoethanolammonium lactate is directly proportional to the log reduction.

Experiment 5

The hand wash here is a preferred hand wash containing optional ingredients that are generally appreciated for their beneficial properties in hand wash formulations. The production process involves dissolving pcmx in dipropylene glycol, saponifying the lauric acid with monoethanolamine, and adding the remaining ingredients to the water.

| Chemical | Amount | Supplier |
|---|---|---|
| Water | q.s. to 100 g | — |
| Ethyl Alcohol | 10 g | Grain Processing Corp., USA |
| Lauric Acid | 5 g | Proctor & Gamble, USA |
| Monoethanolamine | 3.833 g | Equistar Chemicals, USA |
| Dipropylene Glycol | 3 g | Huntsman, USA |
| Lactic Acid 90% USP | 2.733 g | Purac, USA |
| Polozamer 124 | 1 g | BASF, USA |
| PCMX | 0.505 g | Netchem Inc, Canada |
| Versene 100 | 0.5 g | BASF, USA |
| Methyl Paraben | 0.3 g | RITA Corp., USA |
| Propyl Paraben | 0.3 g | RITA Corp., USA |
| Sodium Metabisulfite | 0.1 g | Esseco General Chemistry, USA |

The sample was then inoculated into samples containing a microorganism in duplicate. One of the two samples was neutralized at 15 seconds and the second at 30 seconds. The samples were then plated and incubated for later counting. The data are represented below.

| Microorganism | ATCC Num. | Exposure Time | $Log_{10}$ Reduction | Percent Reduction |
|---|---|---|---|---|
| Acinetobacter baumannii | 19606 | 15 sec. | 4.1775 | 99.9934 |
| Campylobacter jejuni | 29428 | 15 sec. | 5.0453 | 99.9991 |
| Citrobacter freundii | 8090 | 15 sec. | 4.1351 | 99.9927 |
| Clostridium perfringens | 13124 | 15 sec. | 6.9345 | 99.9999 |
| Enterococcus faecalis | 51575 | 15 sec. | 6.2822 | 99.9999 |
| | | 30 sec. | 6.2822 | 99.9999 |
| Enterococcus faecium | 51559 | 15 sec. | 5.8921 | 99.9999 |
| | | 30 sec. | 5.8921 | 99.9999 |
| Escherichia coli | 11229 | 15 sec. | 3.7889 | 99.9837 |
| Escherichia coli | 43888 | 15 sec. | 3.7520 | 99.9823 |
| Klebsiella pneumoniae | 13883 | 15 sec. | 3.6385 | 99.9770 |
| Listeria monocytogenes | 7644 | 15 sec. | 6.5378 | 99.9999 |
| Pseudomonas aeruginosa | 15442 | 15 sec. | 3.7818 | 99.9235 |
| Salmonella choleraesuis | 13076 | 15 sec. | 4.0550 | 99.9912 |
| Salmonella cholerasius | 14028 | 15 sec. | 3.9138 | 99.9878 |
| Shigella dysenteriae | 13313 | 15 sec. | 3.9217 | 99.9880 |
| Shigella sonnei | 11060 | 15 sec. | 3.9004 | 99.9874 |

-continued

| Microorganism | ATCC Num. | Exposure Time | $\text{Log}_{10}$ Reduction | Percent Reduction |
|---|---|---|---|---|
| Staphylococcus aureus | 6538 | 15 sec. | 6.0645 | 99.9999 |
| | | 30 sec. | 6.0645 | 99.9999 |
| Staphylococcus aureus | 33591 | 15 sec. | 1.9860 | 98.9672 |
| | | 30 sec. | 2.3486 | 99.5519 |

The sample has broad spectrum, quick acting activity against these 17 tested organism.

In light of the foregoing, it should thus be evident that the process of the present invention, providing an antimicrobial hand wash, substantially improves the art. While only the preferred embodiments of the present invention have been described in detail hereinabove, the present invention is not to be limited thereto or thereby. Rather, the scope of the invention shall include all modifications and variations that fall within the scope of the attached claims.

The invention claimed is:

1. A process for preparing an antimicrobial hand wash comprising the steps of:
    combining a fatty acid with a nitrogenous base to produce a soap and an excess of base;
    neutralizing the excess base with a neutralizing acid selected from the group consisting of acetic acid, lactic acid, glycolic acid, acetylsalicylic acid, nicotinic acid, benzoic acid, isopropanoic acid, oxalic acid, succinic acid, benzoic acid anhydride, mixed phosphoanhydride, and mixtures thereof.

2. The process of claim 1, wherein the fatty acid is selected from the group consisting of fatty acids derived from crude fats and carboxylic acids having from 6 to 40 carbon atoms in the main fatty chain.

3. The process of claim 1, wherein the fatty acid is selected from the group consisting of arachidic acid, arachidonic acid, beeswax acid, behenic acid, capric acid, caproic acid, caprylic acid, C10-40 hydroxyalkyl acid, C32-36 isoalkyl acid, coconut acid, corn acid, cottonseed acid, erucic acid, hydrogenated coconut acid, hydrogenated menhaden acid, hydrogenated palm acid, hydrogenated tallow acid, hydroxystearic acid, isomerized linoleic acid, isomerized safflower acid, isostearic acid, lauric acid, linoleic acid, myristic acid, oleic acid, olive acid, palm acid, palmitic acid, palm kernel acid, peanut acid, pelargonic acid, rapeseed acid, rice bran acid, ricinoleic acid, safflower acid, soy acid, stearic acid, sunflower seed acid, tall oil acid, tallow acid, undecanoic acid, undecylenic acid, wheat germ acid, and mixtures thereof.

4. The process of claim 1, wherein the nitrogenous base is selected from the group consisting of 2-aminobutanol, aminoethyl propanediol, aminomethyl propanol, aminopropanediol, bis-hydroxyethyl tromethamine, butyl diethanolamine, butylethanolamine, dibutyl ethanolamine, diethanolamine, diisopropanolamine, diisopropylamine, dimethyl isopropanolamine, monoethanolamine, dimethyl monoethanolamine, ethyl ethanolamine, isopropanolamine, isopropylamine, methylethanolamine, methylglucamine, morpholine, triethanolamine, triisopropanolamine, tromethamine, and mixtures thereof.

5. The process of claim 1, wherein the mole to mole ratio of the nitrogenous base to fatty acid is from about 1.5:1 to 3:1.

6. The process of claim 1, further comprising the step of adding a phenol-based antimicrobial agent to the soap.

7. The process of claim 6, wherein the antimicrobial agent is selected from the group consisting of triclosan, 2,2'-dihydroxy-5,5'-dibromodiphenyl ether, p-chloro-m-xylenol, ortho-phenylphenol, and mixtures thereof.

8. The process of claim 1, wherein the fatty acid is lauric acid, the nitrogenous base is monoethanolamine, and the neutralizing acid is lactic acid.

* * * * *